(12) United States Patent
Heide et al.

(10) Patent No.: US 9,173,986 B2
(45) Date of Patent: Nov. 3, 2015

(54) BLOOD TREATMENT UNIT FOR AN EXTRA-CORPOREAL BLOOD TREATMENT APPARATUS

(75) Inventors: Alexander Heide, Eppstein (DE); Christoph Wiktor, Gelnhausen (DE); Arne Peters, Bad Homburg (DE)

(73) Assignee: Fresenius Medical Care Deutschland GmbH, Bad Homburg (DE)

( * ) Notice: Subject to any disclaimer, the term of this patent is extended or adjusted under 35 U.S.C. 154(b) by 596 days.

(21) Appl. No.: 13/347,836

(22) Filed: Jan. 11, 2012

(65) Prior Publication Data

US 2012/0175295 A1  Jul. 12, 2012

Related U.S. Application Data

(60) Provisional application No. 61/431,447, filed on Jan. 11, 2011.

(30) Foreign Application Priority Data

Jan. 11, 2011  (DE) .......................... 10 2011 008 329

(51) Int. Cl.
*B01D 61/28* (2006.01)
*B01D 61/20* (2006.01)
(Continued)

(52) U.S. Cl.
CPC ............... *A61M 1/26* (2013.01); *A61M 1/1006* (2014.02); *A61M 1/267* (2014.02); *B01D 61/20* (2013.01);
(Continued)

(58) Field of Classification Search
CPC ..... A61M 1/26; A61M 1/1006; A61M 1/267; A61M 1/101; A61M 1/3413; B01D 2313/243; B01D 2325/08; B01D 61/20; B01D 61/30; B01D 63/06; B01D 61/22; B01D 61/32
USPC ......... 210/134, 143, 252, 257.2, 258, 321.63, 210/321.69, 433.1
See application file for complete search history.

(56) References Cited

U.S. PATENT DOCUMENTS 3,771,658 A   11/1973   Brumfield
4,212,741 A    7/1980   Brumfield
(Continued)

FOREIGN PATENT DOCUMENTS

DE    20 52 119 B    4/1972
DE    3923692 A1    1/1991
(Continued)

OTHER PUBLICATIONS

Hoeltzenbein, Josef, Die Kuenstliche Niere-Apparative and klinische Grundlagen der extrakorporalen Haemodialyse. Stuttgart: Ferdinand Enke, 1969. 85. ISBN X-00000000001.
International Preliminary Report on Patentability from PCT/EP2012/000073, mailed on Jul. 25, 2013.

*Primary Examiner* — John Kim
(74) *Attorney, Agent, or Firm* — Kenyon & Kenyon LLP

(57) ABSTRACT

The housing of the blood treatment unit according to the invention holds both a blood pump and a semi-permeable membrane. The blood pump is an impeller pump. The impeller of the impeller pump is surrounded by a partition which divides the housing into two chambers. The semi-permeable membrane forms at least a part of the partition. It is therefore possible for an exchange of matter to take place between the blood which flows through the first chamber of the housing and the dialysis fluid which flows through the second chamber of the housing. The blood treatment unit is intended for an extra-corporeal blood treatment apparatus and has a particularly compact construction.

18 Claims, 3 Drawing Sheets

(51) Int. Cl.
  *B01D 61/22* (2006.01)
  *A61M 1/16* (2006.01)
  *A61M 1/26* (2006.01)
  *B01D 61/32* (2006.01)
  *B01D 61/30* (2006.01)
  *B01D 63/06* (2006.01)
  *A61M 1/10* (2006.01)
  *A61M 1/34* (2006.01)

(52) U.S. Cl.
  CPC ............... *B01D 61/22* (2013.01); *B01D 61/30* (2013.01); *B01D 61/32* (2013.01); *B01D 63/06* (2013.01); *A61M 1/101* (2013.01); *A61M 1/3413* (2013.01); *B01D 2313/243* (2013.01); *B01D 2325/08* (2013.01)

(56) References Cited

U.S. PATENT DOCUMENTS

| | | | | |
|---|---|---|---|---|
| 4,661,246 A | * | 4/1987 | Ash | 210/87 |
| 5,211,849 A | * | 5/1993 | Kitaevich et al. | 604/5.04 |
| 5,783,085 A | | 7/1998 | Fischel | |
| 7,871,566 B2 | * | 1/2011 | Strauss et al. | 422/45 |
| 8,647,569 B1 | * | 2/2014 | Federspiel et al. | 422/45 |

FOREIGN PATENT DOCUMENTS

| | | |
|---|---|---|
| DE | 103 41 221 A1 | 3/2005 |
| EP | 0 576 677 A1 | 1/1994 |
| EP | 1930034 A1 | 6/2008 |
| EP | 2 295 133 A1 | 3/2011 |
| WO | 93/05828 | 4/1993 |

* cited by examiner

BLOOD TREATMENT UNIT FOR AN EXTRA-CORPOREAL BLOOD TREATMENT APPARATUS

CROSS REFERENCE TO RELATED APPLICATIONS

This application claims priority to U.S. Provisional Application No. 61/431,447 filed Jan. 11, 2011 and to German Patent Application No. DE 10 2011 008 329.4 filed Jan. 11, 2011, both of which are incorporated fully by reference herein.

FIELD OF THE INVENTION

The present invention relates to a blood treatment unit for an extra-corporeal blood treatment apparatus having an extra-corporeal blood circuit, which has an arterial blood line for the infeed of blood and a venous blood line for the outfeed of blood. The present invention also relates to an extra-corporeal blood treatment apparatus that has the blood treatment unit according to the present invention.

BACKGROUND OF THE INVENTION

For the extra-corporeal treatment of blood, there are various processes which are used for removing substances needing to be excreted and for extracting fluid. In hemodialysis, the patient's blood is cleansed outside the body in a dialyser. The dialyser has a blood chamber and a dialysis-fluid chamber which are separated by a semi-permeable membrane. During the treatment, to enable the blood to be cleansed effectively, the patient's blood flows through the blood chamber while dialysis fluid flows through the dialysis-fluid chamber.

In hemodialysis (HD), the movement (diffusion) of the substances of low molecular weight through the semi-permeable membrane of the dialyser is governed essentially by the differences in concentration between the blood and the dialysis fluid. In hemofiltration (HF), fluid is extracted from the blood, through the membrane (ultrafiltration), by means of a pressure gradient that is applied to the semi-permeable membrane (a trans-membrane pressure). Hemodiafiltration is a process for the extra-corporeal treatment of blood in which both hemodialysis and hemofiltration are carried out.

The exchange of matter that takes place during the extra-corporeal blood treatment takes place in the dialyser. The form of dialyser most frequently used is the capillary dialyser which comprises a housing in which a large number of hollow fibers are arranged in parallel. The blood flows within the hollow fibers whereas the dialysis fluid flows along the outside of the bundle of hollow fibers. To increase the effectiveness of the transfer of matter, the blood and the dialysis fluid flow in counter-current. An extra-corporeal blood treatment apparatus for hemodialysis, hemofiltration and hemodiafiltration will be referred to in what follows as a dialysis apparatus.

The known pieces of dialysis apparatus have peristaltic pumps by which the blood is pumped through the dialyser in the extra-corporeal blood circuit.

Known from DE 39 23 692 A1 is a medical apparatus for the exchange of matter and heat between a liquid and a treatment medium, in which the pump pumping the treatment medium and the blood treatment unit are arranged one behind the other in an elongated housing. The tubular housing comprises a pump chamber having a pump impeller and a space in which is situated a bundle of hollow fibers whose hollow fibers extend in the longitudinal direction of the tubular housing. As it rotates, the pump impeller pumps the treatment medium through the hollow fibers of the bundle of hollow fibers while a liquid flows round the bundle of hollow fibers.

In the field of blood oxygenation, impeller pumps are used to pump the blood. In oxygenating blood, blood circulating in an extra-corporeal blood circuit is brought into contact with oxygen through a selective membrane. Bundles of hollow fibers are also used as selective membranes. However, in contrast to dialysis, what flows through the hollow fibers is not blood but the treatment medium (oxygen), while the blood flows along the outside of the hollow fibers.

There are various known types of impeller pumps. The particularly distinctive feature of impeller pumps is that they have an impeller which is surrounded by an annular or tubular housing.

WO 93/05828 and EP 1 930 034 A1 describe impeller pumps for blood oxygenation. The two impeller pumps are characterised in that the blood is pumped along the outside of the bundle of hollow fibers by the impeller of the impeller pump while the oxygen flows through the hollow fibers.

SUMMARY OF THE INVENTION

The object underlying the present invention is to specify an alternative to the dialysers and blood pumps of the known pieces of extra-corporeal dialysis apparatus.

The blood treatment unit according to the present invention is intended for an extra-corporeal dialysis apparatus. It is distinguished by being of particularly compact construction, thus making it suitable even for portable dialysis units. The extra-corporeal blood circuit of the dialysis apparatus can be considerably reduced in size with the blood treatment unit according to the present invention.

The housing of the blood treatment unit according to the present invention holds both the blood pump and the semi-permeable membrane of the dialyser of the extra-corporeal dialysis apparatus. Although what will be discussed below is one common housing for the blood pump and the semi-permeable membrane, it is also possible for the housing to comprise a plurality of parts, such as, for example, as two halves of the housing which are releasably connected together.

The blood pump is an impeller pump, the impeller being mounted in the housing to be rotatable on an axis. The impeller is surrounded by a partition which divides the housing into two chambers. Because the semi-permeable membrane forms at least a part of the partition, it is possible for an exchange of matter to take place between the blood which flows through the first chamber of the housing and the dialysis fluid which flows through the second chamber thereof.

Although the blood treatment unit according to the present invention may be of relatively small dimensions, the impeller pump, which can be operated at a high speed of revolution, allows effective dialysis treatment to be given. Because of the high speed of revolution of the impeller pump, the blood which is pumped by the pump flows through the first chamber repeatedly before it leaves the chamber again. The flow of blood against the interface of the membrane is thus particularly effective.

Hence, what is crucial to the overall size of the blood treatment unit according to the present invention is not only the semi-permeable membrane (dialyser) but also the speed of revolution and diameter of the impeller of the impeller pump. Because impeller pumps are generally operated at a high speed of revolution and are of relatively small dimensions, it is possible for a blood treatment unit of compact construction to be provided.

The blood treatment unit according to the present invention can be used not only for hemodialysis but also for hemofiltration. However, for hemofiltration, dialysis fluid does not flow through the second chamber of the housing. The blood treatment unit according to the present invention can also be used for hemodiafiltration.

The semi-permeable membrane of the blood treatment unit according to the present invention may be composed of the known filtering materials for dialysis membranes. Typical semi-permeable filtering materials are based on polysulphone or cellulose acetate. It is however also possible for PTFE membranes, membranes of polycarbonate or even ceramic membranes to be used. It is equally possible for use to be made of membranes made of semiconductive materials which are produced by micro-structuring techniques or etching processes.

In another embodiment of blood treatment unit according to the present invention, the housing has an inlet duct for the infeed of blood which runs to the first chamber and which extends in the direction defined by the axis of rotation of the impeller. Consequently, the blood is fed to the first chamber in the axial direction. The housing preferably has an outlet duct, running away from the first chamber, for the outfeed of blood, which outlet duct extends in the radial direction. Consequently, the blood is fed in in the axial direction and pumped, by means of the rotating impeller, in the direction of the membrane surrounding the impeller, the blood, having flowed around the membrane repeatedly in the first chamber, being fed out of the chamber again in the radial direction.

A particularly compact construction is obtained if the outlet duct for the outfeed of blood passes through the semi-permeable membrane in the radial direction, effectiveness being highest when the semi-permeable membrane surrounds the impeller completely except for the region occupied by the outlet duct.

The housing preferably has an inlet duct running to the second chamber for the infeed of dialysis fluid and an outlet duct running away from the second chamber for the outfeed of dialysis fluid. The blood treatment unit according to the present invention can thus be used not only for hemofiltration but also for hemodialysis.

The second chamber of the housing preferably takes the form of an annular space which preferably completely surrounds the first chamber of the housing, with the semi-permeable membrane separating the first and second chambers from one another. If the semi-permeable membrane were to form only parts of the partition separating the housing into the first and second chambers, the second chamber would preferably surround that region of the partition in which the semi-permeable membrane was situated. The chambers and the membrane are preferably so designed and arranged that there is incident flow against the entire area of the membrane from both sides.

In another which is a particular preference, the semi-permeable membrane is provided with grooves on the surface adjacent the first chamber. The grooves may take the form of longitudinal and/or transverse grooves. With the longitudinal and/or transverse grooves present, the red blood corpuscles are able to align themselves in the center of these flow ducts by the Fahraeus-Lindqvist effect and to produce an increased proportion of plasma at the filtering surface.

The extra-corporeal dialysis apparatus according to the present invention has the blood treatment unit according to the present invention. It also has an arterial blood line for feeding blood into the first chamber of the blood treatment unit and a venous blood line for feeding blood out of the first chamber thereof. The extra-corporeal dialysis apparatus may also have an infeed line for dialysis fluid and an outfeed line for dialysis fluid for feeding dialysis fluid respectively into and out of the second chamber of the blood treatment unit.

It is of advantage that the ultrafiltration rate can be controlled easily by throttling the flow of blood in the blood outfeed line. A preferred embodiment of extra-corporeal dialysis apparatus therefore provides means for throttling the flow of blood which are arranged in the blood outfeed line. It is crucial for a trans-membrane pressure differential to be generated. A trans-membrane pressure differential may for example be generated by means of throttling members on the blood side which cause a build-up of pressure by reducing the flow of blood. Such means may for example be a controllable valve. The pressure differential may also be built up by a second pump which acts in the opposite direction to that in which the impeller pumps. The generation of the pressure differential may also be performed by means present on the dialysis-fluid side, such for example as by an additional ultrafiltration pump which generates a pressure below the pressure on the blood side.

Another embodiment of extra-corporeal dialysis apparatus which is a particular preference has a control unit which is so designed that the blood pump and/or the dialysis-fluid pump can be operated in a pulsed mode. What is distinctive about the pulsed mode is that the blood or dialysis-fluid pump is switched on and off continuously or the speed of revolution of the pumps is varied, i.e. increased and decreased, continuously. The operation of the blood pump in the pulsed mode is able to benefit the diffusion processes at the membrane. The operation of the dialysis-fluid pump may also have a positive influence on the filtering effect because the pores of the filter are "flushed" cyclically by the pulses of pressure on the dialysate side.

Two embodiments of the present invention will be explained in detail in what follows by reference to the drawings.

DETAILED DESCRIPTION OF THE DRAWINGS

Figure 1:
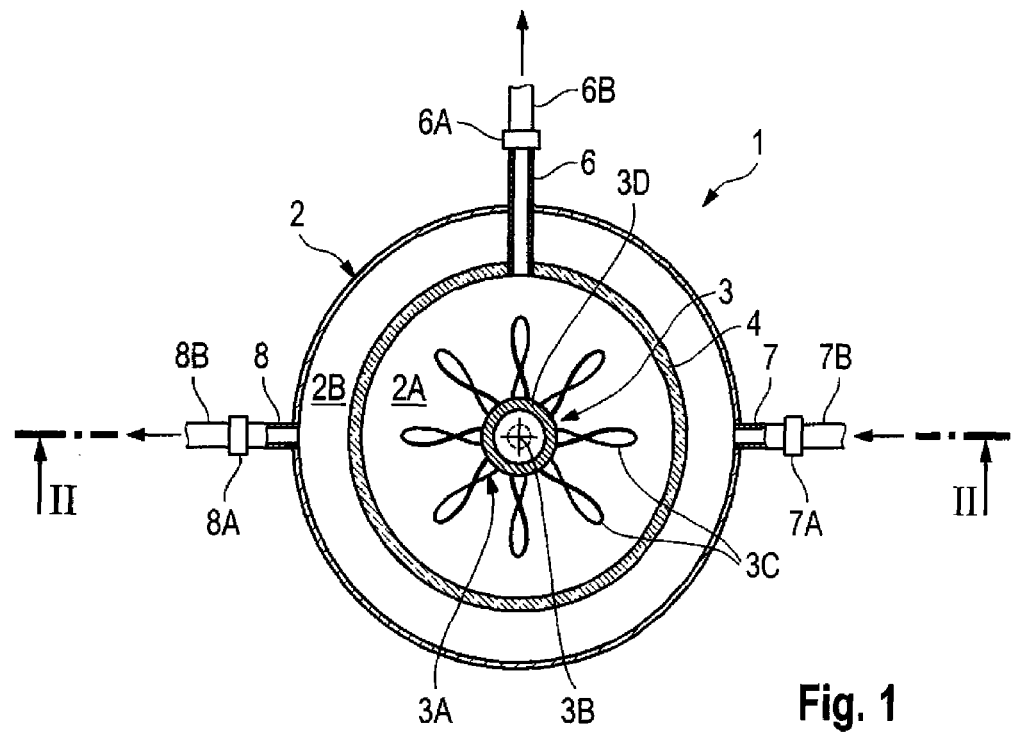
FIG. 1 is a highly simplified schematic view of a first embodiment of blood treatment unit according to the present invention.
Figure 2:
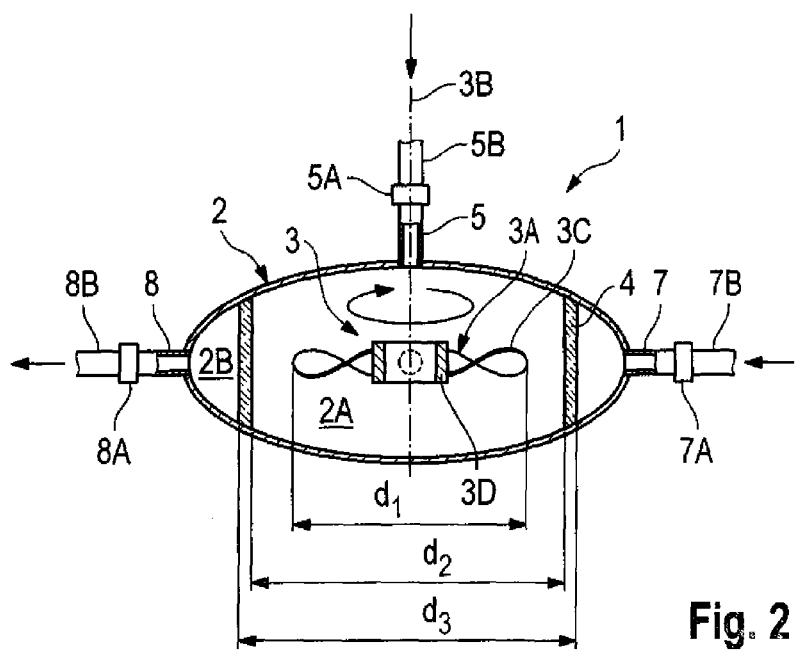
FIG. 2 is a section on line II-II in FIG. 1.

FIGS. 1 and 2 are highly simplified schematic views showing the blood treatment unit according to the present invention in section. The blood treatment unit 1 has a cylindrical housing 2 which may comprise two housing halves which are screwed together. Situated in the cylindrical housing 2 is a blood pump 3. The blood pump is an impeller pump 3. The impeller pump 3 has an impeller 3A which is mounted in the housing to be rotatable on an axis 3B. The impeller 3A may be mounted in the housing 2 mechanically, electro-magnetically, hydrodynamically or hydrostatically. It has a plurality of propeller blades, vanes or wing tips 3C which extend outwards from the center. A drive unit 3D, which may for example be an electro-magnetic, pneumatic or mechanical drive, is provided to drive the impeller 3A. The outside diameter of the impeller 3A is shown as $d_1$.

The impeller 3A is surrounded by a semi-permeable membrane 4 which extends around the impeller 3A for an angle of 360° in the circumferential direction. The membrane 4 has an inside diameter $d_2$ and an outside diameter $d_3$. The thickness of the membrane is $d_3-d_2$. The inside diameter $d_2$ of the semi-permeable membrane 4 and the outside diameter $d_1$ of the impeller 3A are of a size such that a gap is left between the impeller and the membrane.

The semi-permeable membrane 4 divides the cylindrical housing 2 into a first, inner, chamber 2A and a second, outer, chamber 2B. The semi-permeable membrane 4 therefore forms, in the housing 2, a partition between the two chambers 2A and 2B.

The housing 2 has an axial inlet duct 5 which extends through the wall of the housing in the direction defined by the axis of rotation 3B of the impeller 3A. At the inlet of the inlet duct 5 there is a connecting piece 5A for connecting on a blood infeed line 5B which is merely indicated. As well as this, the housing 2 also has a radial outlet duct 6 for the outfeed of blood which extends through the wall of the housing in the radial direction and passes through the semi-permeable membrane 4. At the outlet of the outlet duct 6 is a connecting piece 6A for connecting on a blood outfeed line 6B which is merely indicated.

When the impeller 3A rotates, blood is drawn into the first chamber 2A in the axial direction via the inlet duct 5. Due to the rotation of the impeller 3A, the blood flows repeatedly along the inner circumference of the semi-permeable membrane 4, in the first chamber 2A, before it leaves the first chamber 2A again via the outlet duct 6.

The second chamber 2B of the housing 2 forms an annular space which completely surrounds the outside of the semi-permeable membrane 4.

As well as the inlet and outlet ducts 5, 6 for feeding blood in and out, there is also formed in the housing 2 an inlet duct 7 for feeding dialysis fluid into the second chamber 2B and an outlet duct 8 for feeding dialysis fluid out of the second chamber. Situated at the inlet of the inlet duct 7 and the outlet of the outlet duct 8 are connecting pieces 7A and 8A respectively for connecting on dialysis-fluid infeed and outfeed lines 7B and 8B respectively, which are merely indicated. The inlet and outlet ducts 7, 8 for feeding dialysis fluid respectively in and out are so arranged that, in the annular space, the dialysis fluid flows along the outer surface of the semi-permeable membrane 4.

Thus, while the blood treatment unit 1 is operating, blood and dialysis fluid flow along the inner side and outer side respectively of the semi-permeable membrane 4. Consequently, flow takes place around the semi-permeable membrane 4 from both sides. It may be advantageous for the flow characteristics in this case if the semi-permeable membrane 6 has on the inner side fine longitudinal and/or transverse grooves which may be of a depth of approximately 50 μm.

The thickness of the semi-permeable membrane 4 may be from 1 to 10 mm. It may comprise a functional membrane layer and a layer providing mechanical support, with the functional layer providing the filtration effect needed for the therapy, which filtration effect is determined by the parameters important for the therapy, and in particular by the sieving coefficient, the hydraulic permeability and bio-compatibility. The functional layer may be of thicknesses from 15 to 100 μm.

The impeller pump 3 may for example be operated at a speed of revolution of approximately 7000 rpm. In the present embodiment the outside diameter $d_2$ of the impeller is 30 mm and the semi-permeable membrane 4 is of a thickness $d_3-d_2$ of 10 mm in the embodiment.

Figure 3:
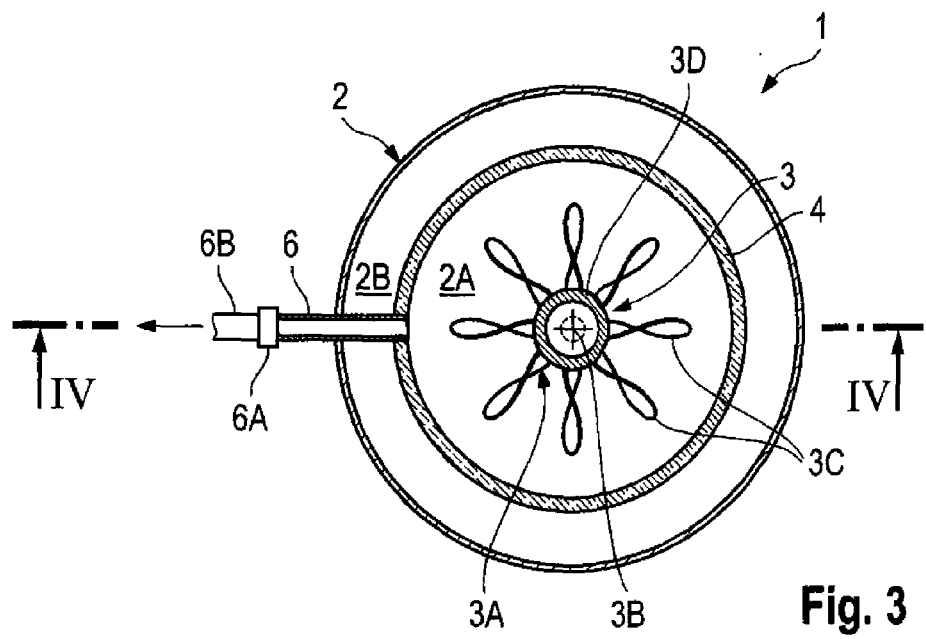
FIG. 3 is a highly simplified schematic view of a second embodiment of blood treatment unit according to the present invention.
Figure 4:
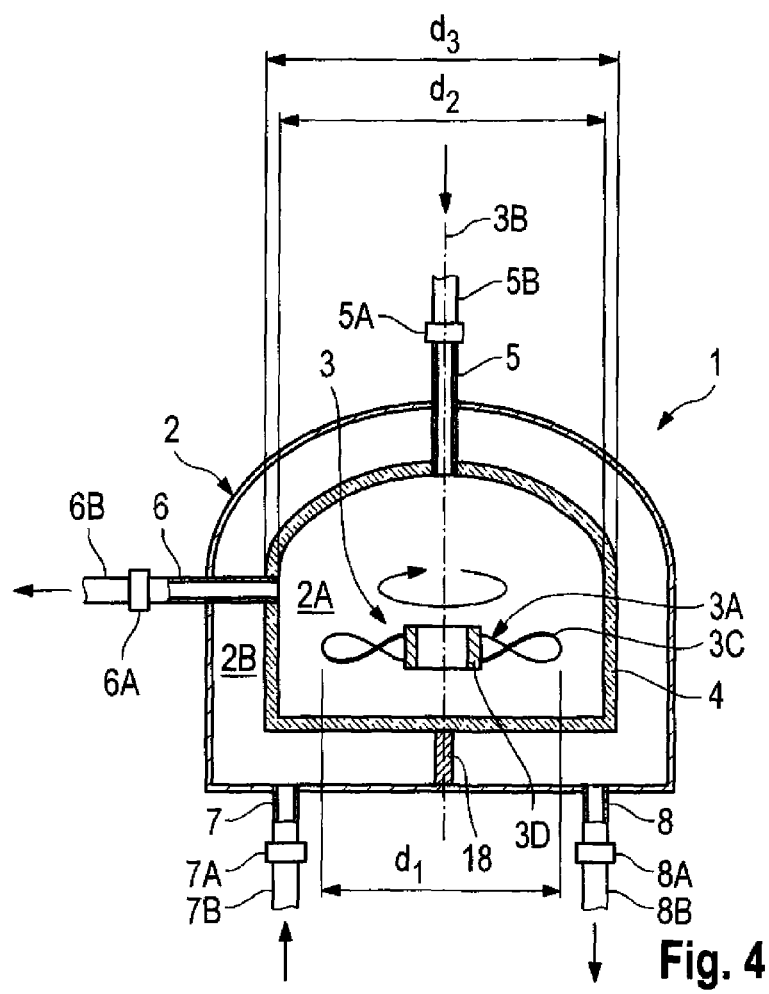
FIG. 4 is a section on line IV-IV in FIG. 3.

FIGS. 3 and 4 are highly simplified schematic views showing a second embodiment of blood treatment unit according to the present invention. The second embodiment differs from the first embodiment only in the shape of the housing. Parts which correspond to one another are therefore designated by the same reference numerals.

In the second embodiment, the blood is drawn into the first chamber 2A of the housing 2 by the rotating impeller 3 in the axial direction, via the inlet duct 5, before then leaving the housing again in the radial direction via the outlet duct 6. Dialysis fluid also once again flows through the second chamber 2B of the housing 2, being fed in via the inlet duct 7 and out via the outlet duct 8. A partition 18 which is arranged between the inlet duct 7 and the outlet duct 8 and which extends between the inner wall of the housing 2 and the outer wall of the membrane 4 prevents the dialysate from flowing in a shunt between the connections. In the second embodiment, not only is the outer circumferential surface of the impeller 3A surrounded by the semi-permeable membrane 4 and the second chamber 2B of the housing but the semi-permeable membrane 4 also surrounds the impeller 3 on all sides. The second chamber 2B of the housing 2 takes the form of a space which surrounds the semi-permeable membrane 4 on all sides in the second embodiment. The effective area of the membrane in the second embodiment is thus larger than in the first embodiment.

The use that is made of the blood treatment unit 1 according to the present invention in an extra-corporeal dialysis apparatus will be described below. Only the principal components of the dialysis apparatus which will be described.

Figure 5:
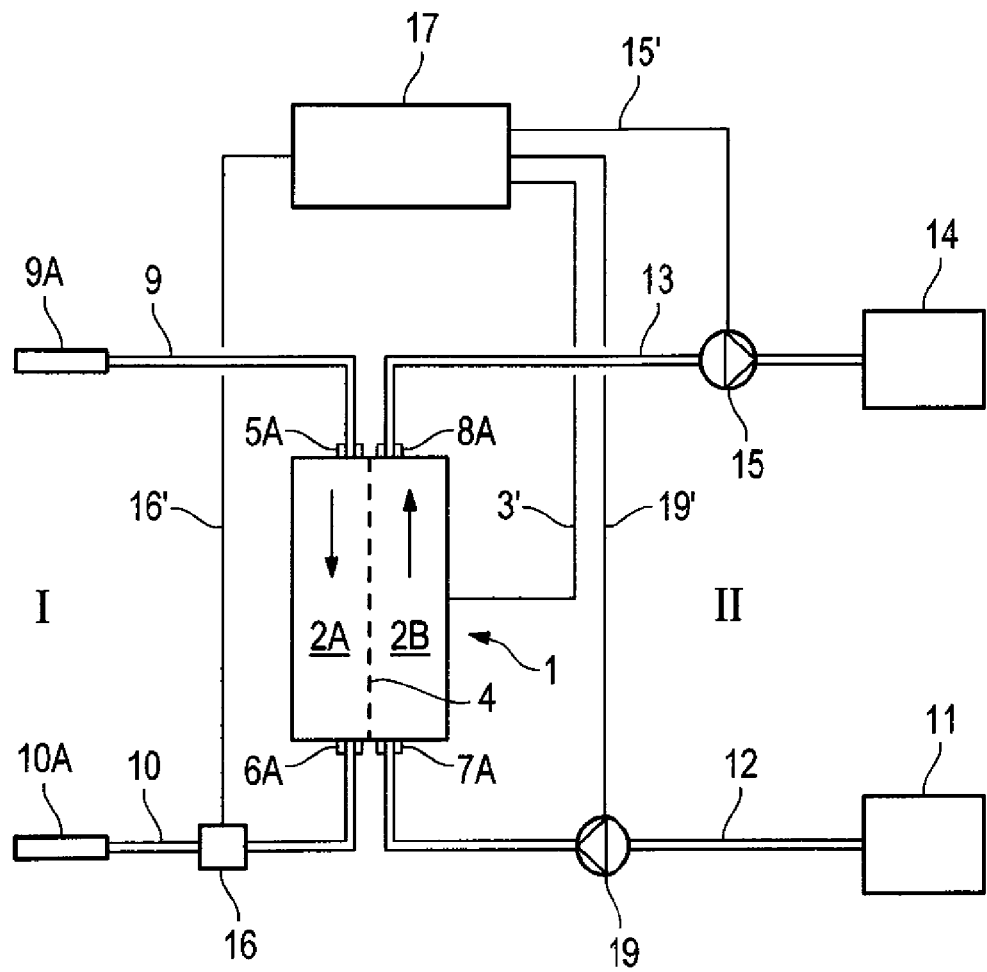
FIG. 5 is a highly simplified schematic view of an embodiment of extra-corporeal dialysis apparatus which has the blood treatment unit according to the present invention.

FIG. 5 is a highly simplified schematic view showing the principal components of the extra-corporeal dialysis apparatus which has the blood treatment unit 1 according to the present invention. The dialysis apparatus has an arterial blood line 9 and a venous blood line 10. Situated at one end of the arterial blood line is an arterial patient connection 9A (needle), while the other end of the arterial blood line 9 is connected to the connecting piece 5A on the inlet duct 5 to the first chamber 2A of the blood treatment unit 1. The venous blood line 10 has a venous patient connection 10A (needle) at one end, while the other end of the venous blood line 10 is connected to the connecting piece 6A on the outlet duct 6 from the first chamber 2A of the blood treatment unit 1 (FIGS. 1 to 4). From a source 11 of dialysis fluid, a dialysis-fluid infeed line 12 runs to the connecting piece 7A on the inlet duct 7 to the second chamber 2B of the blood treatment unit 1. A dialysis-fluid outfeed line 13, which leads to a discharge 14, runs from the connecting piece 8A on the outlet duct 8 from the second chamber 2B of the blood treatment unit. Arranged in the dialysis-fluid outfeed line 13 is a pump 15 which acts as an ultrafiltration pump, while in the arterial blood line 10 there is a controller 16 for throttling the flow of blood, which may be an electro-magnetically actuatable flow controller 16. The dialysis fluid is pumped by a dialysis-fluid pump 19 which is arranged in the dialysis fluid infeed line 12 upstream of the blood treatment unit 1.

As well as this, the dialysis apparatus also has a central control unit 17 which is connected by control lines 3', 15', 16', 19' to the impeller pump 3 (not shown in FIG. 5) of the blood treatment unit 1, to the ultrafiltration pump 15, to the electro-magnetically actuatable flow controller 16 and to the dialysis-fluid pump 19.

During dialysis, the impeller pump 3 of the blood treatment unit 1 pumps the patient's blood through the first chamber 2A of the blood treatment unit 1 in the extra-corporeal blood circuit I, while the dialysis-fluid pump 19 pumps dialysis fluid through the second chamber 2B of the blood treatment unit in counter-current in the dialysis-fluid circuit II, thus enabling an exchange of matter to take place between the blood and dialysis fluid.

The ultrafiltration rate can be set by varying the speed of revolution of the impeller pump and the trans-membrane pressure at the semi-permeable membrane 4 of the blood treatment unit 1. The relative pressures can be varied with the flow controller 16 or the ultrafiltration pump 15, which can each be controlled by the control unit 17. The ultrafiltration pump 15 serves in this case as a means of increasing the trans-membrane pressure differential by causing a drop in the pressure in the dialysis-fluid chamber relative to the pressure in the blood chamber. The trans-membrane pressure differential may however equally well be increased by raising the pressure in the blood chamber.

It may prove advantageous for the control unit 17 to operate the impeller pump 3 and/or the dialysis-fluid pump 19 in a pulsed mode in order to produce a discontinuous flow of blood and dialysis fluid respectively. This may for example be achieved by switching one or both the pumps 3, 15 on and off continuously or by continuously increasing or decreasing the pumping rate of one or both pumps. An alternative way in which this pulsed mode is also possible is by actuating valves arranged in the lines.

The extra-corporeal dialysis apparatus according to the present invention is distinguished by a compact construction because the blood pump and dialyser of the dialysis apparatus are combined into one unit which, due to the relatively small dimensions of the dialyser membrane, can be accommodated in a relatively small housing.

What is claimed is:

1. A blood treatment unit for an extra-corporeal blood treatment apparatus, comprising:
    a housing having a first chamber and a second chamber;
    an impeller pump comprising an impeller rotatably mounted in the housing, said impeller pump being surrounded by a partition dividing the housing into the first chamber and the second chamber; and
    a semi-permeable membrane forming at least a part of the partition,
    wherein the semi-permeable membrane enables an exchange of matter to take place between a first fluid in the first chamber and a second fluid in the second chamber,
    wherein the first fluid is blood and the second fluid is a dialysis fluid, wherein the second chamber of the housing is an annular space which completely surrounds an outer wall of the semi-permeable membrane.

2. The blood treatment unit according to claim 1, wherein the housing further comprises an inlet duct for the infeed of blood to the first chamber, said inlet duct extending in a direction defined by an axis of rotation of the impeller.

3. The blood treatment unit according to claim 2, wherein the housing further comprises an outlet duct for the outfeed of blood from the first chamber, said outlet duct extending in a radial direction.

4. The blood treatment unit according to claim 3, wherein the outlet duct passes through the semi-permeable membrane in the radial direction.

5. The blood treatment unit according to claim 1, wherein the housing further comprises an inlet duct for the infeed of dialysis fluid to the second chamber.

6. The blood treatment unit according to claim 5, wherein the housing further comprises an outlet duct for the outfeed of dialysis fluid from the second chamber.

7. The blood treatment unit according to claim 1, wherein the second chamber completely surrounds the first chamber.

8. The blood treatment unit according to claim 7, wherein the semi-permeable membrane has grooves on a surface adjacent the first chamber.

9. An extra-corporeal blood treatment apparatus, comprising:
    a blood treatment unit comprising:
        a housing having a first chamber and a second chamber;
        an impeller pump comprising an impeller rotatably mounted in the housing, said impeller pump being surrounded by a partition dividing the housing into the first chamber and the second chamber; and
        a semi-permeable membrane forming at least a part of the partition,
        wherein the semi-permeable membrane enables an exchange of matter to take place between a first fluid in the first chamber and a second fluid in the second chamber,
        wherein the first fluid is blood and the second fluid is a dialysis fluid;
    wherein the extra-corporeal blood treatment apparatus is a dialysis apparatus comprising:
        an arterial blood line for feeding blood into the first chamber of the blood treatment unit, and a venous blood line for feeding blood out of the first chamber of the blood treatment unit,
    wherein the second chamber of the housing is an annular space which completely surrounds an outer wall of the semi-permeable membrane.

10. The extra-corporeal blood treatment apparatus according to claim 9, wherein the blood treatment apparatus further comprises:
    an infeed line for feeding dialysis fluid into the second chamber of the blood treatment unit, and an outfeed line for feeding dialysis fluid out of the second chamber of the blood treatment unit.

11. The extra-corporeal blood treatment apparatus according to claim 10, further comprising a device blood pump arranged in the arterial blood line.

12. The extra-corporeal blood treatment apparatus according to claim 11, further comprising a dialysis-fluid pump arranged in the dialysis-fluid infeed line.

13. The extra-corporeal blood treatment apparatus according to claim 12, further comprising a control unit that is configured to operate the blood pump, the dialysis-fluid pump, or both in a pulsed mode in which the blood pump, the dialysis-fluid pump, or both is switched on and off continuously or the speed of revolution of the blood pump, the dialysis-fluid pump, or both is increased and decreased continuously.

14. The blood treatment unit according to claim 4, wherein the housing further comprises an inlet duct for the infeed of dialysis fluid to the second chamber.

15. The blood treatment unit according to claim 14, wherein the housing further comprises an outlet duct for the outfeed of dialysis fluid from the second chamber.

16. The extra-corporeal blood treatment apparatus according to claim 10, further comprising a dialysis-fluid pump arranged in the dialysis-fluid infeed line.

17. The blood treatment unit according to claim 9, wherein the second chamber completely surrounds the first chamber.

18. The blood treatment unit according to claim 9, wherein the semi-permeable membrane has grooves on a surface adjacent the first chamber.

\* \* \* \* \*